(12) United States Patent
Ishibashi et al.

(10) Patent No.: US 10,556,098 B2
(45) Date of Patent: Feb. 11, 2020

(54) MICRONEEDLE ARRAY COATED WITH DRUG COMPOSITION

(71) Applicants: TEIJIN LIMITED, Osaka (JP);
MEDRX CO., LTD, Kagawa (JP)

(72) Inventors: Masaki Ishibashi, Kagawa (JP);
Hidetoshi Hamamoto, Kagawa (JP);
Taishi Tanaka, Hiroshima (JP);
Kazuteru Kouno, Tokyo (JP);
Kiyotsuna Toyohara, Tokyo (JP)

(73) Assignee: MEDRX CO., LTD., Kagawa (JP)

( * ) Notice: Subject to any disclaimer, the term of this patent is extended or adjusted under 35 U.S.C. 154(b) by 432 days.

(21) Appl. No.: 14/424,840

(22) PCT Filed: Aug. 30, 2013

(86) PCT No.: PCT/JP2013/073386
§ 371 (c)(1),
(2) Date: Feb. 27, 2015

(87) PCT Pub. No.: WO2014/034882
PCT Pub. Date: Mar. 6, 2014

(65) Prior Publication Data
US 2015/0216796 A1    Aug. 6, 2015

(30) Foreign Application Priority Data

Aug. 30, 2012 (JP) ................................ 2012-190693

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 39/00* (2013.01); *A61K 47/38* (2013.01); *A61K 2039/54* (2013.01)

(58) Field of Classification Search
CPC ...... A61M 37/0015; A61M 2037/0023; A61M 2037/0046; A61M 2037/0053; A61K 9/0021
See application file for complete search history.

(56) References Cited

U.S. PATENT DOCUMENTS

2004/0049150 A1* 3/2004 Dalton ................. A61B 17/205
604/46
2004/0062813 A1* 4/2004 Cormier ............... A61K 9/0021
424/489
(Continued)

FOREIGN PATENT DOCUMENTS

JP    2007-536988 A    12/2007
WO   2005/112984 A2   12/2005
(Continued)

OTHER PUBLICATIONS

International Preliminary Report on Patentability and Written Opinion issued in corresponding International Patent Application No. PCT/JP2013/073386 dated Mar. 12, 2015.
(Continued)

*Primary Examiner* — Kami A Bosworth
(74) *Attorney, Agent, or Firm* — Morgan, Lewis & Bockius LLP

(57) ABSTRACT

The present disclosure relates to a microneedle array having a pin frog shape which is coated with a drug composition comprising a drug and an additive and having Vickers hardness of about 3 or more is applied to a microneedle array. The microneedle array coated with the drug composition according to the present invention can be used in the field in which the drug is required to be administered with high quantitative performance even when the drug is contained at low content.

18 Claims, 5 Drawing Sheets

(51) Int. Cl.
*A61K 39/00* (2006.01)
*A61K 47/38* (2006.01)

(56) References Cited

U.S. PATENT DOCUMENTS

| | | | |
|---|---|---|---|
| 2007/0299388 A1* | 12/2007 | Chan | A61K 9/0021 604/46 |
| 2009/0017210 A1* | 1/2009 | Andrianov | A61M 37/0015 427/256 |
| 2010/0221314 A1 | 9/2010 | Matsudo et al. | |
| 2011/0059150 A1* | 3/2011 | Kendall | A61K 9/0021 424/423 |
| 2011/0288485 A1 | 11/2011 | Tokumoto et al. | |
| 2012/0330250 A1* | 12/2012 | Kuwahara | A61M 37/0015 604/272 |
| 2013/0006217 A1* | 1/2013 | Hattersley | A61K 38/29 604/506 |
| 2013/0144230 A1* | 6/2013 | Wu | A61F 13/0216 604/319 |
| 2013/0287832 A1* | 10/2013 | O'Hagan | A61B 17/205 424/426 |
| 2013/0296790 A1* | 11/2013 | Masaoka | A61M 37/0015 604/173 |

FOREIGN PATENT DOCUMENTS

| | | |
|---|---|---|
| WO | 2009/051147 A1 | 4/2009 |
| WO | 2010/074239 A1 | 7/2010 |
| WO | 2010/143689 A1 | 12/2010 |
| WO | 2011/119584 A1 | 9/2011 |

OTHER PUBLICATIONS

International Search Report issued in corresponding International Patent Application No. PCT/JP2013/073386 dated Oct. 15, 2013.
Office Action issued in corresponding Japanese Patent Application No. 2014-533127 dated Aug. 29, 2017 (see partial English translation).

* cited by examiner

MICRONEEDLE ARRAY COATED WITH DRUG COMPOSITION

TECHNICAL FIELD

The present invention relates to a coated microneedle array. Particularly, the present invention relates to a microneedle array which can accurately inject a small amount of a drug such as a vaccine into the skin.

BACKGROUND ART

Recently, a microneedle array has been frequently tried to be used as one of transdermal administration methods of a drug. Along with the popularization of a microneedle array, various attempts to fix a drug on a microneedle array have been made. In general, a microneedle array supporting a drug is prepared by dissolving a drug in a solvent and coating a microneedle array with the drug solution. However, when a microneedle array made of a biodegradable polylactic acid resin (PLA) or polyglycolic acid resin (PGA) is coated with a drug solution (e.g. an aqueous solution), it is essential to add an additive which acts as a polymeric tackifier to the solution to attach the drug on the surface of the microneedle array. For example, Patent Document 1 discloses that polysaccharides which are compatible with a drug (such as pullulan and hydroxypropylcellulose) can be used as a carrier for coating. Furthermore, Patent Document 2 discloses that preferred examples of a carrier for loading a drug on a microneedle array made of PLA include pullulan, carboxyvinylpolymer and the like.

Also, Patent Document 3 discloses that preferred examples of a carrier for loading follicle-stimulating hormone and the like on a microneedle array made of PLA include pullulan and sucrose which are compatible (i.e., uniformly soluble).

A carrier (i.e., an additive) used for coating a microneedle array is required to assure the same safety as that of an aqueous preparation for injection, and thus an additive available here is highly restricted. In many instances, the polysaccharides as shown in the above Patent Documents 1-3 are used as the carrier. Furthermore, the viscosity of a drug solution varies depending on the property of an additive used, and thus the amount of the loaded drug should be adjusted depending on the different viscosity. Also, as doing re-coating of a drug solution on a microneedle array, the drug attaches on the needle tip, which might cause the blunting of the needle tip of a microneedle array, and thus the puncturability of the microneedle array is supposed to be less.

Thus, in order to accurately inject a small amount of a drug into the skin along with maintaining the puncturability of a microneedle array, it is required to select a suitable additive. Although a variety of means for maintaining the puncturability of a microneedle array and effectively injecting a small amount of a drug such as a vaccine into the skin have been studied, any useful solutions have not been found yet.

PRIOR ART DOCUMENTS

Patent Document 1: WO 2009/051147
Patent Document 2: WO 2010/143689
Patent Document 3: WO 2010/074239

SUMMARY OF INVENTION

Problem to be Solved by the Invention

An object of the present invention is to provide a microneedle array which can be inserted into the skin without reducing the puncturability of the microneedle array even when the microneedle array is coated with a drug, and without removing the loaded drug when the microneedle array is inserted into the skin. Furthermore, another object of the present invention is to provide a composition for coating the microneedle array.

Means for Solving the Problems

Until now, the present inventors have studied the method that a microneedle array having an excellent puncturability (cf. WO 2012/057345, etc.) is immersed in a drug solution and dried, and then microneedles of the microneedle array are coated with the drug solution (cf. WO 2012/057602). In order to load and attach a drug on a microneedle array, it is required to use not only a drug but also an additive for providing a drug solution with a given viscosity. However, the amount of an additive needs to increase with increasing the amount of a drug loaded on a microneedle array. Thus, even though a microneedle array has an excellent puncturability, there have been some problems, for example, a drug loaded on the microneedle array might cause blunting of the tip part of microneedles, and the drug loaded on the microneedle array might be removed out.

With respect to such problems, the present inventors supposed that, when the amount of a drug to be loaded was 50 to 250 µg per 100 microneedles, the tip part of microneedles could be less blunted because there is not so great change in the shape of microneedles due to the coating, and also a drug loaded on the microneedles could be hardly removable. The present inventors have been done various studies on a drug composition which is hardly removable from a microneedle array in the range of such coating amount. As a result, as shown in FIG. 2, it has been found that, when the hardness (the Vickers hardness) of a drug composition is about 3 or more, the amount of the drug composition removed from the microneedle array is smaller, and thus excellent puncture and insertion into the skin can be achieved. Specifically, the present inventors have found that the puncturability of the microneedle array coated with a drug composition and the insertability of a drug into the skin can be evaluated by measuring the hardness of the loaded drug composition using the Vickers hardness as an index.

Furthermore, the present inventors have found that the Vickers hardness of the loaded drug composition varies depending on the type of a drug used, even when using the same additive, as shown in FIG. 1. On the other hand, FIG. 9 shows that the Vickers hardness of the loaded drug composition is less affected by the type of an additive when using the same drug (compared with the Vickers hardness of OVA in FIG. 1), accordingly it has been clarified that the Vickers hardness is more affected by the type of a drug.

Through the above finding, it has become possible to classify an additive (i.e., an additive as an adhesive additive or as a hardness-imparting additive) by evaluating the Vickers hardness. Thereby, the present inventors have found that it is possible to adjust a desired hardness by combining any two types of additives. As a result, the decrease in the hardness by the addition of a drug can be improved, and the Vickers hardness of a drug composition can be adjusted to about 3 or more. Based on the finding that such control on a microneedle array can be made by using the Vickers hardness, the present inventors have found that the puncturability of a microneedle array coated with a drug composition can be well fixed regardless of the type of a drug, and thus the drug can be effectively injected into the skin.

The present inventors have completed the present invention on the basis of the above findings.

The subject matters of the present invention are as follows.

(1) A microneedle array coated with a drug composition comprising a drug and additive(s), wherein the drug composition after being loaded and dried has a Vickers hardness of 3 or more, and the amount of the loaded drug composition is 50 to 250 μg per 100 microneedles.

(2) The microneedle array according to the above item (1), wherein said Vickers hardness is 10 or more.

(3) The microneedle array according to the above item (1), wherein said Vickers hardness is 12 or more.

(4) The microneedle array according to the above item (1), wherein said additive is an additive having a Vickers hardness of 10 or more which acts as a hardness-imparting additive or an additive having a Vickers hardness of 3 to 10.

(5) The microneedle array according to the above item (1), wherein said additive is an additive-mixture of an additive having a Vickers hardness of 10 or more which acts as a hardness-imparting additive and an additive having a Vickers hardness of 3 to 10.

(6) The microneedle array according to the above item (4) or (5), wherein said additive having a Vickers hardness of 3 to 10 is sodium carboxymethylcellulose.

(7) The microneedle array according to the above item (1), wherein said additive is an additive-mixture of an additive having a Vickers hardness of less than 3 which acts as an adhesive additive and an additive having a Vickers hardness of 10 or more which acts as a hardness-imparting additive, or an additive-mixture of an additive having a Vickers hardness of less than 3 and an additive having a Vickers hardness of 3 to 10.

(8) The microneedle array according to the above item (7), wherein said additive having a Vickers hardness of less than 3 which acts as an adhesive additive is at least one selected from the group consisting of hydroxypropylcellulose, sorbitol, and trehalose.

(9) The microneedle array according to any one of the above items (4) to (8), wherein said additive having a Vickers hardness of 10 or more which acts as a hardness-imparting additive is at least one selected from the group consisting of dextran, gelatin, collagen, and hyaluronic acid.

(10) The microneedle array according to the above item (1), wherein said additive is at least one selected from the group consisting of sugar or a derivative thereof, collagen, gelatin, and polyvinylpyrrolidone.

(11) The microneedle array according to the above item (10), wherein said sugar or a derivative thereof is at least one selected from the group consisting of hydroxypropylcellulose, sodium carboxymethylcellulose, hyaluronic acid, trehalose, lactose, sucrose, sorbitol, pullulan, and dextran.

(12) The microneedle array according to any one of the above items (1) to (11), wherein said drug is a peptide, a protein, a nucleic acid, or RNA.

(13) The microneedle array according to any one of the above items (1) to (12), wherein said drug is a vaccine.

(14) The microneedle array according to any one of the above items (1) to (13), wherein the amount of said drug is 25 w/w % or less.

(15) The microneedle array according to any one of the above items (1) to (14), wherein the amount of the additive which acts as an adhesive additive is 5 to 20 w/w % relative to the total amount of said additive-mixture.

(16) A method of preparing a drug-loaded microneedle array, which comprises coating a microneedle array with a solution of a drug composition comprising a drug and an additive and drying it, wherein the amount of the loaded drug composition after being loaded and dried is 50 to 250 μg per 100 microneedles, and the loaded and dried drug composition has a Vickers hardness of 3 or more.

(17) The method according to the above item (16), wherein said Vickers hardness is 10 or more.

(18) The method according to the above item (16), wherein said Vickers hardness is 12 or more.

(19) The method according to the above item (16), wherein said additive is an additive having a Vickers hardness of 10 or more which acts as a hardness-imparting additive or an additive having a Vickers hardness of 3 to 10.

(20) The method according to the above item (16), wherein said additive is an additive-mixture of an additive having a Vickers hardness of 10 or more which acts as a hardness-imparting additive and an additive having a Vickers hardness of 3 to 10.

(21) The method according to the above item (19) or (20), wherein said additive having a Vickers hardness of 3 to 10 is sodium carboxymethylcellulose.

(22) The method according to the above item (16), said additive is an additive-mixture of an additive having a Vickers hardness of less than 3 which acts as an adhesive additive and an additive having a Vickers hardness of 10 or more which acts as a hardness-imparting additive, or an additive-mixture of an additive having a Vickers hardness of less than 3 and an additive having a Vickers hardness of 3 to 10.

(23) The method according to the above item (22), wherein said additive having a Vickers hardness of less than 3 which acts as an adhesive additive is at least one selected from the group consisting of hydroxypropylcellulose, sorbitol, and trehalose.

(24) The method according to any one of the above items (19) to (23), wherein said additive having a Vickers hardness of 10 or more which acts as a hardness-imparting additive is at least one selected from the group consisting of dextran, gelatin, collagen, and hyaluronic acid.

(25) The method according to the above item (16), wherein said additive is at least one selected from the group consisting of sugar or a derivative thereof, collagen, gelatin, and polyvinylpyrrolidone.

(26) The method according to the above item (25), wherein said sugar or a derivative thereof is at least one selected from the group consisting of hydroxypropylcellulose, sodium carboxymethylcellulose, hyaluronic acid, trehalose, lactose, sucrose, sorbitol, pullulan, and dextran.

(27) The method according to any one of the above items (16) to (26), wherein said solution is an aqueous solution.

(28) The method according to any one of the above items (16) to (27), wherein said drying step is performed at a temperature of 30° C. or less.

(29) The method according to any one of the above items (16) to (28), wherein said drug is a peptide, a protein, a nucleic acid, or RNA.

(30) The method according to any one of the above items (16) to (29), wherein said drug is a vaccine.

(31) A method of preparing a microneedle array on which a drug composition having a desired Vickers hardness is loaded, comprising the steps of:

1) combining an additive which acts as a hardness-impairing additive and an additive which acts as an adhesive additive to prepare an aqueous solution of an additive-mixture wherein the additive which acts as an adhesive additive is 20 w/w % or less;

2) adding a drug in the total amount of 25 w/w % or less into the aqueous solution of the additive-mixture to prepare an aqueous solution of a drug composition;

3) loading and drying said drug composition solution on a test piece, and measuring the Vickers hardness of the drug composition; and 4) coating the microneedle array with the drug composition solution and drying it, if said Vickers hardness is a desired hardness.

(32) The method according to the above item (31), wherein the amount of said additive which acts as an adhesive additive is 5 to 20 w/w % relative to the total amount of the additive-mixture.

(33) The method according to the above item (31) or (32), wherein said additive which acts as an adhesive additive is selected from hydroxypropylcellulose, trehalose, or sorbitol.

(34) The method according to any one of the above items (31) to (33), wherein said additive which acts as a hardness-imparting additive is at least one selected from the consisting of sodium carboxymethylcellulose, hyaluronic acid, gelatin, collagen, and dextran.

Effects of the Invention

The drug-loaded microneedle array of the present invention relates to a microneedle array wherein a drug composition has a Vickers hardness of about 3 or more, and is strongly loaded on a microneedle array. The drug composition can endure friction on puncture into the skin to be accurately inserted into the skin with the microneedle array, and thus the amount of a drug to be required can be accurately injected into the skin. As a result, the microneedle array coated with the drug composition of the present invention can be used in the fields in which the drug is required to be administrated with high quantitative performance even when the drug is contained in small amounts, for example, the administration of a vaccine, and the scope of application of the microneedle array can be extended.

Furthermore, it has become possible to classify an additive (i.e., an additive as an adhesive additive or as a hardness-imparting additive) by evaluating the Vickers hardness. Thus, a desired hardness can be maintained by combining any two types of additives, and the decrease in the hardness by the addition of a drug can be corrected. That is, the Vickers hardness of the drug composition can be adjusted to a suitable hardness by conditioning a combination of additives regardless of the type of a drug. As a result, the puncturability of the microneedle array coated with a drug of the present invention can be always adjusted to be in good condition regardless of the type of a drug.

BRIEF DESCRIPTION OF DRAWINGS

FIG. 1 shows that the variation in the Vickers hardness differs greatly between small molecular compounds (lidocaine hydrochloride and metoclopramide) and ovalbumin which is a high molecular compound (OVA, a molecular weight of about 45,000). Also, FIG. 1 shows that for the same small molecular compounds, the Vickers hardness in case of metoclopramide can be more easily decreased.

FIG. 2 shows that the Vickers hardness can increase with the increase in the amount of OVA, and converges to the Vickers hardness of OVA itself.

FIG. 3 shows that a puncture rate of 90% or more can be achieved by a Vickers hardness of 3 or more.

FIG. 8 shows the change in the rat's blood levels at the time. The change in the blood levels suggests that desmopressin acetate injected into the skin rapidly transferred in the blood.

BEST MODE FOR CARRYING OUT THE INVENTION

—First Embodiment of the Present Invention—

Figure 1:
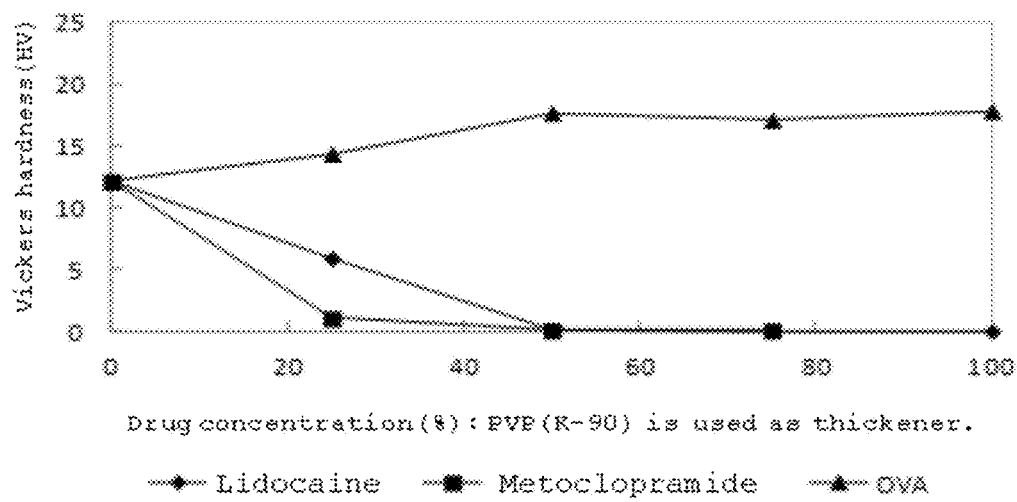
FIG. 1 is a diagram showing that the Vickers hardness of the drug composition is affected by the type of a drug in combination with an additive.

The first embodiment of the present invention relates to a microneedle array coated with a drug composition comprising a drug and an additive.

The term "microneedle array" in the present invention means a microneedle array having 50 to 200 microneedles with a height of 300 to 1000 μm per $cm^2$. The microneedle array used herein can be made of a material comprising a resin, a ceramics, and a metal. Furthermore, the material of the microneedle array is preferably a material comprising a thermoplastic resin, and more preferably a material comprising a biodegradable thermoplastic resin. It is expected that such material can be easily produced on a large scale, and can adequately assure the safety in use.

In the present invention, the preferred moiety of the microneedle array for loading a drug is closer to the tip of microneedles. In addition, it is preferable that a drug is loaded on a microneedle array so as not to lack a sharpness of the tip part of microneedles. In order to coat a microneedle array with a drug in such condition, for example, a method of immersing a microneedle array in grooves filled with a drug solution (WO 2010/056702) can be used. The amount of the loaded drug and the position of the coating can be properly regulated by controlling the immersion depth (the coated range of a microneedle array). For example, microneedles in a microneedle array are preferably coated from the top to 400 μm therefrom. When the amount of the loaded drug is small, it is enough to coat the microneedles from the tip to 100 μm therefrom.

The microneedle array of the present invention can be prepared according to known preparation methods. For example, the microneedle array of the present invention can be prepared according to WO 2012/057345.

The term "Vickers hardness" in the present invention is defined by Japanese Industrial Standards (JIS B7225, Z2244), and means the hardness calculated from the indentation load on providing an indentation generated by pressing a test piece with an indenter made of quadrilateral diamond with an angle of 136° between the opposite faces, and the surface area obtained from the length of the diagonal line. In the present invention, the Vickers hardness was measured with a micro-Vickers tester (MVK-G2500 manufactured by Akashi Seisakusho, Ltd.). As a result shown in FIG. 3, when the Vickers hardness of a drug composition is about 3 or more, about 90% of the drug composition loaded on the microneedle array can be injected into the skin without being removed from the microneedle array. Also, when the Vickers hardness of a drug composition is about 10 or more, about 95% of the drug composition loaded on the microneedle array can be injected into the skin without being removed from the microneedle array. Furthermore, when the Vickers hardness of a drug composition is about 12 or more, most of the loaded drug composition can be injected into the skin without being removed from the microneedle array.

The term "drug" in the present invention is not especially limited as long as it is used as a medicament which is a liquid drug itself or can be an aqueous solution with a solvent such as a hydrophilic solvent. Particularly, the preferred drug is a physiologically active ingredient which achieves a pharmaceutical effect in small amounts. Examples of the drug include a peptide, a protein, a nucleic acid, and RNA. Examples of the drug include proteins such as desmopressin, interferon, erythropoietin, follitropin, G-CSF, GM-CSF, human chorionic gonadotropin, luteinizing hormone, calcitonin, glucagon, insulin, and human growth hormone. Also, the drug includes Japanese encephalitis vaccine, rotavirus vaccine, diphtheria vaccine, pertussis vaccine, *Diplococcus pneumoniae* vaccine, tuberculosis vaccine, rubella vaccine, measles vaccine, herpesvirus vaccine, and DNA vaccine.

Furthermore, when a drug is a small molecular compound, a small molecular compound can be used as a hydrochloride salt of a basic drug or an alkali metal salt of carboxylic acid, phosphoric acid, or sulfonic acid drug, which has high water solubility. Particularly, the basic drug is not limited as long as it has high water solubility. Examples of the basic drug include lidocaine hydrochloride, morphine hydrochloride, and metoclopramide hydrochloride. Also, amongst examples of the small molecular compound having an alkali metal salt of carboxylic acid, phosphoric acid, or sulfonic acid, for example, the compound having carboxylic acid include non-steroidal antiphlogistic analgesics such as indometacin and diclofenac, oligopeptides such as a vaccine, and proteins. The compound having phosphoric acid include a nucleic acid, an oligonucleotide, and RNA. The compound having sulfonic acid include carbazochrome sulfonic acid.

Suitable amount of the drug is defined in each drug. For example, the amount of the drug may be 25 w/w % or less, for example, 1-25 w/w %, 1-20 w/w % or 1-10 w/w %, relative to the amount of the drug composition. Also, the amount of the drug may be, for example, 0.01 to 10000 μg, 0.1 to 1000 μg, 0.1 to 100 μg or 0.1 to 10 μg, per 100 microneedles of the microneedle array.

In the "additive" of the present invention, one or more additives selected from the group consisting of cellulose-type additives such as hydroxypropylcellulose, hydroxymethylcellulose, and sodium carboxymethylcellulose; protein-type additives such as albumin, casein, gelatin, and collagen; alginic acid; agar; starch; and sugar or a derivative thereof such as hydroxypropylcellulose, sodium carboxymethylcellulose, hyaluronic acid, trehalose, lactose, sucrose, sorbitol, pullulan, and dextran can be used as a natural additive. Also, additives such as polyvinylalchol compounds, polyacrylic acid compounds, polyglycolic acid compounds, polyamide compounds, polyester compounds, and polyvinylpyrrolidone (PVP) can be used as a synthetic additive.

The preferred additive of the present invention is an additive which has high affinity with a biological body and desirable property such as less dermal irritation. Thus, the use of a natural additive is particularly preferable. Preferred examples of the natural additive include protein-type additives such as collagen and gelatin. Examples of the sugar and a derivative thereof include sodium carboxymethylcellulose, hydroxypropylcellulose, trehalose, sucrose, lactose, fructose, galactose, mannose, maltose, glucose, mannitol, and pullulan, and more preferably trehalose, lactose, sucrose, and pullulan. As the particularly preferred additive, an additive-mixture consisting of various additives prepared by combining sodium carboxymethylcellulose and hydroxypropylcellulose having a high molecular weight, and polyvinylpyrrolidone with other sugar or a derivative thereof can be used.

Figure 4:
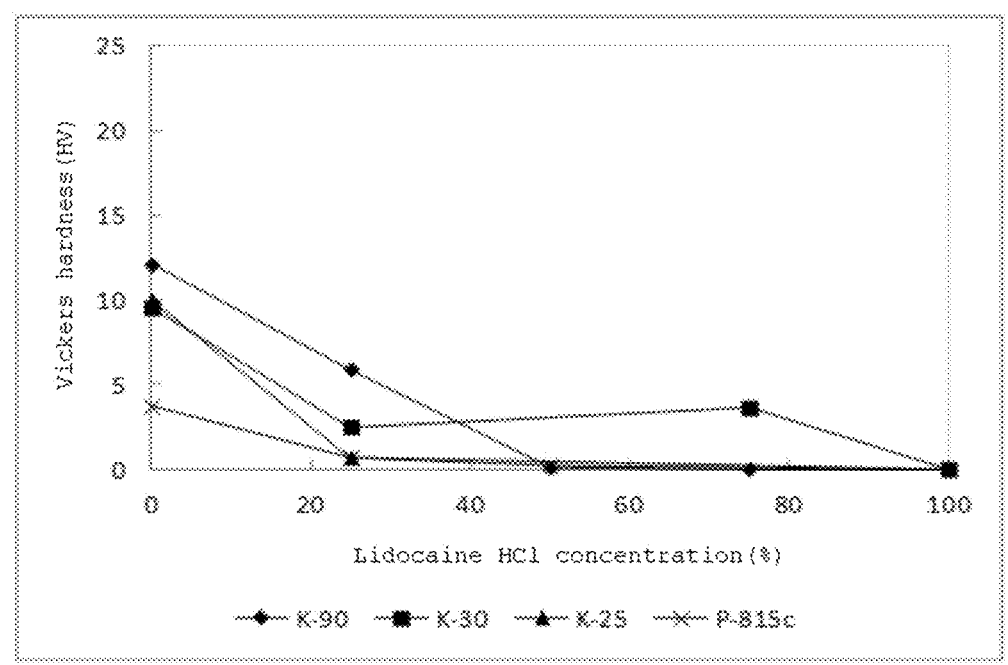
FIG. 4 is a diagram showing that the Vickers hardness of the drug (lidocaine hydrochloride) composition is affected by the combinations of the drug and some types of additives. Comparing PVPs (K-90, K-30, and K-25) and sodium carboxymethylcellulose (P-815c), it is expected that the drug composition having low Vickers hardness can be easily prepared by using sodium carboxymethylcellulose.
Figure 9:
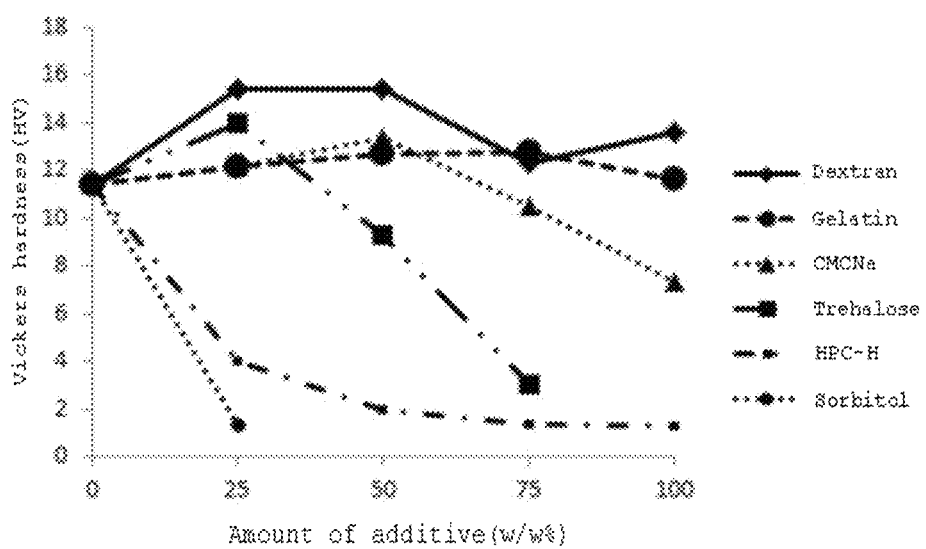
FIG. 9 is a diagram showing the results of Table 1 in Example 1. The present inventors have studied how the Vickers hardness of the drug composition which comprises OVA as a drug after the coating and drying processes varies depending on the amount of the drug and the type of the additive. For the sake of simplicity, the Vickers hardness in two-component system of a drug and an additive was measured.

In order to obtain the desirable property in the drug composition of the present invention, a combination of additives and a combination of an additive and a drug as well as the amount of each ingredient can be adjusted using the Vickers hardness as an index to prepare suitable drug composition. For example, as shown in FIG. 1 and FIG. 4, the Vickers hardness of the drug composition greatly varies depending on a combination of the drug and the additive to be used. When a high molecular weight drug with water solubility is used, the Vickers hardness of a drug composition has a tendency to be relatively highly preserved regardless of the amount of a drug, and thus the amount of the loaded drug can be increased. Also, as shown in FIG. 9, the Vickers hardness of the drug composition has a tendency to show almost the same change regardless of the type of the additive as long as the drug used is the same. Furthermore, the present inventors have found that the Vickers hardness of a drug composition can also be adjusted by combining various additives.

Also, molecular weight and distribution coefficient (log P) of a drug can be used as an additional index of the present invention. When a high molecular weight drug with water-solubility, for example, a drug having a molecular weight of more than 800, preferably more than 1000 and a distribution coefficient of less than −2.5 is used, a microneedle array having a desirable property can be provided. Regarding a low molecular weight drug with water-solubility, for example, a drug having a molecular weight of less than 500 can be used in the present invention regardless of the distribution coefficient.

In order to prepare a drug composition having desired Vickers hardness by experimenting on various combinations of additives, for example, the Vickers hardness of a drug composition obtained by coating a glass plate with a part of an aqueous solution of a drug composition and drying it is measured. When a drug composition has a low Vickers hardness, the hardness of the drug composition can be adjusted by the addition of an additive having higher hardness to increase the hardness. For example, one or more of additives selected from the group consisting of collagen, gelatin, dextran and the like are added as the additive. A part of an aqueous solution of a drug composition after the addition of the additive is loaded on a glass plate and dried to measure the Vickers hardness of the drug composition again. Thus, the drug composition having a desired Vickers hardness can be prepared by adjusting the amount of an additive having higher hardness to be added while measuring the Vickers hardness.

Also, the present inventors have found that an additive can be classified into two roles of additives by measuring the Vickers hardness of the additive itself. Specifically, the present inventors have found that an additive is classified into an adhesive additive for attaching a drug composition to a microneedle array, and an additive for providing hardness to a drug composition. For example, the present inventors have found that an additive acts as an adhesive additive when the Vickers hardness of the additive itself is less than 3, an additive acts as both an adhesive additive and a hardness-imparting additive when the Vickers hardness is 3 to 10, and an additive acts as a hardness-imparting additive when the Vickers hardness is 10 or more. Examples of the adhesive additive include hydroxypropylcellulose, sorbitol, and trehalose. Examples of the hardness-imparting additive include gelatin, dextran, PVP, collagen, and hyaluronic acid. Examples of the additive having both adhesive property and hardness-imparting property include sodium carboxymethylcellulose (CMCNa). Thus, the desired Vickers hardness of a drug composition can be adjusted by using these additives alone or in combination as described above.

In the present invention, other additives may be used to further adjust the hardness of a drug composition. For example, an additive having lower hardness (e.g. stearic acid) may be added to decrease the hardness of a drug composition. Also, an additive having higher hardness may be added to increase the hardness of a drug composition. As described above, in the present invention, suitable combination of a drug and an additive can be produced using the Vickers hardness as an index. Thus, even though any type of drug is used, a drug composition having a Vickers hardness of 3 or more can be prepared, and thereby a microneedle array which can surely insert the drug into the skin can be prepared.

—Second Embodiment of the Present Invention—

The second embodiment of the present invention relates to a method of preparing a microneedle array coated with a drug composition comprising a drug and an additive. Specifically, the preparation method of the present invention comprises the steps of preparing an additive-mixture by combining a hardness-imparting additive and an adhesive additive using the Vickers hardness as an index, preparing a solution of a drug composition having a desired Vickers hardness by adding a drug and other additives such as an antioxidant thereto and mixing it, and coating a microneedle array with the solution. Briefly, the preparation method of the present invention is a method of preparing a drug-loaded microneedle array having high puncturability by controlling the hardness of a drug composition using the Vickers hardness as an index.

The term "solution" in the present invention is not especially limited as long as it dissolves the drug and the additive used herein. Preferably, the solution is easily volatilizable at ambient temperature. Examples of the solution include water, a hydrophilic solvent, and a mixed solvent thereof. As the hydrophilic solvent, alcohols such as ethyl alcohol and isopropyl alcohol, a miscible amount of organic solvent, for example, ethers such as ether and THF and esters such as ethyl acetate, and a mixed solvent thereof may be added. Preferred examples of the solution include water, and a mixture of water and a hydrophilic solvent. The solution may further comprise additives such as a pH adjuster, an antioxidant, and a preservative as long as the effects of the present invention are not blocked. As the above suitable additives, commercially available reagents may be used for any purpose.

Examples of the pH adjuster include a buffering agent consisting of an organic acid such as citric acid, tartaric acid, lactic acid, fumaric acid, and malic acid and an alkali metal salt thereof, and a buffering agent consisting of an inorganic acid such as phosphoric acid and an alkali metal salt thereof.

Examples of the antioxidant include ascorbic acid, BHT, sodium hydrogen sulfite, sodium sulfite, erythorbic acid, tocopherol acetate, dibutylhydroxytoluene, tocopherol, sodium pyrosulfite, butylhydroxyanisol, and propyl gallate.

Examples of the preservative include benzoic acid, sodium benzoate, sorbin, sodium sorbate, sodium dehydroacetate, paraoxybenzoic acid, sodium paraoxybenzoate, ethyl paraoxybenzoate, propyl paraoxybenzoate (propylparaben), butyl paraoxybenzoate, isopropyl paraoxybenzoate, isobutyl paraoxybenzoate, propionic acid, and sodium propionate.

The term "loading (coating)" in the present invention means that a drug composition is loaded according to a method of immersing the needle tips of a microneedle array in a solution containing said composition for coating. The loading/coating method can be performed according to the known method, for example, the method described in WO 2012/056702.

The terms in this embodiment in common with the first embodiment of the present invention are as defined in the first embodiment.

EXAMPLES

Hereinafter, the present invention will be described more specifically with reference to Examples. However, the present invention is not intended to be limited to them by any means.

Example 1

Evaluation about Hardness of Loaded Drug Composition (1) Evaluation about Contribution of the Drug to the Hardness while Keeping the Additive Constant The following aqueous solution of each drug composition was prepared, and it was loaded on a glass plate and dried. Then, the hardness (the Vickers hardness) of the drug composition was measured with a micro-Vickers tester (MVK-G2500 manufactured by Akashi Seisakusho, Ltd.).

a) Reagent (Aqueous solution of drug composition)
   Additive: Polyvinylpyrrolidone (PVP) K-90
   Drug: Lidocaine (Distribution Coefficient: 2.7), Metoclopramide (Distribution Coefficient: 2.0), or Ovalbumin (OVA)
   Water: Water was added to adjust the concentration of the drug to 0 w/w %, 25 w/w %, 50 w/w %, 75 w/w %, or 100 w/w %.
b) Result:
   The result of the measured Vickers hardness of each drug composition is shown in FIG. 1. Specifically, the result showed that the hardness of a drug composition was greatly affected by the type and amount of a drug to be contained even though the same additive was used. Thus, it was clarified that the hardness of a drug composition could not be clearly predicted from only a combination of an additive and a drug, and the Vickers hardness measurement was necessary for a given hardness.

(2) Evaluation about Contribution of the Additive to the Hardness while Keeping the Drug Constant Ovalbumin (OVA) was used as a drug, and sorbitol, trehalose, dextran, hydroxypropylcellulose H (HPC-H), sodium carboxymethylcellulose (CMCNa), or gelatin was used as an additive. Drug compositions wherein the amount of the additive was 0 w/w %, 25 w/w %, 50 w/w %, 75 w/w %, or 100 w/w % were prepared, and then the Vickers hardness of the drug compositions after being dried was measured in the same manner as the above (1). The result is listed in order that the higher Vickers hardness in the 100% additives is the lower, and is shown in Table 1 below and FIG. 9.

TABLE 1

|  | Amount of additive | | | | |
| --- | --- | --- | --- | --- | --- |
| OVA | 100 w/w % | 75 w/w % | 50 w/w % | 25 w/w % | 0 w/w % |
| Additive | 0 w/w % | 25 w/w % | 50 w/w % | 75 w/w % | 100 w/w % |
| Type of additive | | | | | |
| Sorbitol | 11.4 | 1.4 | — | — | — |
| HPC-H | 11.4 | 4.0 | 2 | 1.4 | 1.3 |
| Trehalose | 11.4 | 14.0 | 9.3 | 3.0 | — |
| CMCNa | 11.4 | 12.2 | 13.4 | 10.5 | 7.3 |
| Gelatin | 11.4 | 12.2 | 12.7 | 12.8 | 11.6 |
| Dextran | 11.4 | 15.4 | 15.4 | 12.3 | 13.6 |

[NOTE]
—: The hardness of the sample is soft, and thus it is difficult to make suitable hardness measurement.

As shown in the above Table 1 and FIG. 9, there was little change in the Vickers hardness of the drug compositions wherein the amount of OVA is 0 to 25 w/w %. Also, considering the result of polyvinylpyrrolidone as shown in FIG. 1, the Vickers hardness of the drug compositions wherein the amount of the drug was 0 to 25 w/w % was little changed from the Vickers hardness in the 100% additive regardless of the type of the additive as long as the drug is the same.

Furthermore, from the result of the measured Vickers hardness in the 100 w/w % additive, it has been found that these additives play two roles in the drug composition. Specifically, the additive can be classified into an adhesive additive for attaching a drug composition to a microneedle array, and an additive for providing hardness to a drug composition. For example, the additive acts as an adhesive additive when the Vickers hardness of the additive itself is less than 3, the additive acts as both an adhesive and a hardness-imparting additives when the Vickers hardness is 3 to 10, and the additive acts as a hardness-imparting additive when the Vickers hardness is 10 or more.

(3) Evaluation of Hardness Change by Combination of Additives

As seen from the above (2), the additives used herein can be classified into two types in use (i.e., one is an adhesive use and the other is a hardness-imparting use). In order to evaluate the change in the Vickers hardness of the drug composition by a combination of an adhesive additive (e.g., sorbitol, HPC-H, and trehalose) and a hardness-imparting additive (e.g., gelatin, and dextran), the Vickers hardness of the compositions in Tables 2 and 3 below was measured.

TABLE 2

| Type of additive | Ratio of two additives | | | | |
| --- | --- | --- | --- | --- | --- |
| Adhesive additive: HPC-H | 40 w/w % | 20 w/w % | 10 w/w % | 5 w/w % | 0 w/w % |
| Hardness-imparting additive: Gelatin | 60 w/w % | 80 w/w % | 90 w/w % | 95 w/w % | 100 w/w % |
| Vickers hardness | 1.3 | 12.6 | 12.2 | 11.8 | 11.6 |

TABLE 3

| Type of additive | Ratio of two additives | | | | |
| --- | --- | --- | --- | --- | --- |
| Adhesive additive: HPC-H | 40 w/w % | 20 w/w % | 10 w/w % | 5 w/w % | 0 w/w % |
| Adhesive additive: Trehalose | 60 w/w % | 80 w/w % | 90 w/w % | 95 w/w % | 100 w/w % |
| Vickers hardness | 1.2 | 0.7 | 0.6 | — | — |

[NOTE]
—: The hardness of the sample is soft, and thus it is difficult to make suitable hardness measurement.

As shown in the above Table 2, it was clarified that when the adhesive additive and the hardness-imparting additive were combined and the amount of the adhesive additive was 20 w/w % or less per the mixture, there was no great change in the Vickers hardness of the additive-mixture. Specifically, the result shows that when the hardness-imparting additive is mainly used and the adhesive additive is added in an amount of 20 w/w % or less to prepare a hard drug composition having a high Vickers hardness, the drug composition can avoid a decrease in the hardness, and thus is suitable as a composition for coating a microneedle array.

Furthermore, it was observed that when the amount of the adhesive additive was increased to 20 to 40 w/w %, the Vickers hardness decreased (i.e., softened) sharply. From this result, it has been found that a suitable additive-mixture having a desired hardness can be prepared by adding an adhesive additive in a range of 20 to 40 w/w % to a hardness-imparting additive.

On the other hand, the Vickers hardness in a combination of adhesive additives remained low.

(4) Effect of the Amount of Drug to be Added to Hardness-Imparting Additive

As shown in FIG. 1, the above (1) shows that when PVP (having a Vickers hardness of about 12) is used as the additive, the Vickers hardness of the drug compositions decreases depending on the increase in the amount of each small molecular compound to be added. Using gelatin having the Vickers hardness similar to that of PVP (the Vickers hardness is 11.6) as the additive, a drug composition comprising lidocaine as a small molecular compound was prepared, and then the change in the hardness of the drug composition was evaluated. Specifically, the present inventors studied the change in the Vickers hardness caused by the difference in the type of the additive when the Vickers hardness of the additive itself was the same. The result is shown in Table 4 below.

TABLE 4

| Drug composition | Composition in drug | | | | |
|---|---|---|---|---|---|
| Lidocaine HCl | 100 w/w % | 75 w/w % | 50 w/w % | 25 w/w % | 0 w/w % |
| Gelatin | 0 w/w % | 25 w/w % | 50 w/w % | 75 w/w % | 100 w/w % |
| Vickers hardness | — | — | — | 4.8 | 11.6 |

[NOTE]
—: The hardness of the sample is soft, and thus it is difficult to make suitable hardness measurement.

As shown in the above Table 4, the addition of lidocaine hydrochloride led to the decrease in the Vickers hardness of the drug composition. This result is similar to that of FIG. 1, i.e., it appears that the Vickers hardness can be changed based on the amount of a drug like the result of FIG. 1, as long as the additive has the same level of the Vickers hardness, regardless of the type of the additive. Specifically, the result shows that when additive having a similar Vickers hardness is used, the Vickers hardness of the drug composition can be determined depending on not the type of the additive but the type and amount of the drug to be added.

As seen from the above, the microneedle array coated with the drug composition having a desired Vickers hardness can be prepared according to the following steps of:

1) combining a hardness-imparting additive and 20 w/w % or less of an adhesive additive to prepare an additive-mixture which maintains the hardness;

2) adding a certain amount of a drug to the additive-mixture, and measuring the Vickers hardness of the drug composition after being loaded and dried;

3) if said Vickers hardness is a desired hardness, coating the microneedle array with the drug composition solution; and 4) if said Vickers hardness is high, adjusting the Vickers hardness to the desired hardness by the addition of further additional adhesive additive, i.e., increasing the amount of the adhesive additive to more than 20 w/w %.

Example 2

Correlation Between Hardness of Drug Composition and Puncture Rate of Microneedle Array In order to evaluate the correlation between the hardness of a drug composition and the puncture rate of a microneedle array, a microneedle array having 97 microneedles (the needle length is about 600 µm) per about 1 $cm^2$ was prepared according to the known method (WO 2012/057345), and the prepared microneedle array was coated with the following drug composition and used herein.

(1) Drug Composition

The aqueous solution of each composition for coating was prepared according to the composition of Table 5 below, and then was loaded on a microneedle array. The isolated rat's skin was punctured with the coated microneedle array, and the microneedle array was pulled out immediately. The microneedle array after the puncture and pull-out was observed with a microscope (Digital Microscope VHX-2000 manufactured by Keyence Corporation). The number of microneedles which were punctured and pulled out without falling away the loaded drug composition was counted, and was expressed as a puncture rate. For the aqueous solution of each drug composition, the measurement was performed in N=3.

TABLE 5

| | I924-1 | I924-2 | I924-3 | I924-4 | I929-1 | I929-2 | I929-3 | I924-5 |
|---|---|---|---|---|---|---|---|---|
| Lidocaine HCl | 0 | 10 | 20 | 30 | 35 | 40 | 45 | 50 |
| OVA | 50 | 40 | 30 | 20 | 15 | 10 | 5 | 0 |
| PVP K-90 | 50 | 50 | 50 | 50 | 50 | 50 | 50 | 50 |
| Purified water | 400 | 400 | 400 | 400 | 400 | 400 | 400 | 400 |
| Total (mg) | 500 | 500 | 500 | 500 | 500 | 500 | 500 | 500 |
| Puncture rate (%) | 98.6 | 92.8 | 91.1 | 62.9 | 59.8 | 59.8 | 42.6 | 17.2 |
| SD | 2.37 | 3.1 | 7.44 | 23.35 | 10.3 | 22.3 | 18.7 | 17.32 |
| Vickers hardness (HV) | 12.13 | 11.3 | 3.19 | 1.86 | 0.42 | 0.21 | 0.077 | 0.08 |
| SD | 1.85 | 1.48 | 0.54 | 0.35 | 0.02 | 0.08 | 0.1 | 0.08 |

[NOTE]
OVA: Ovalbumin (Distribution Coefficient of serum albumin −0.4)
PVP K-90: Polyvinylpyrrolidone K-90

(2) Coating Method

Figure 5:
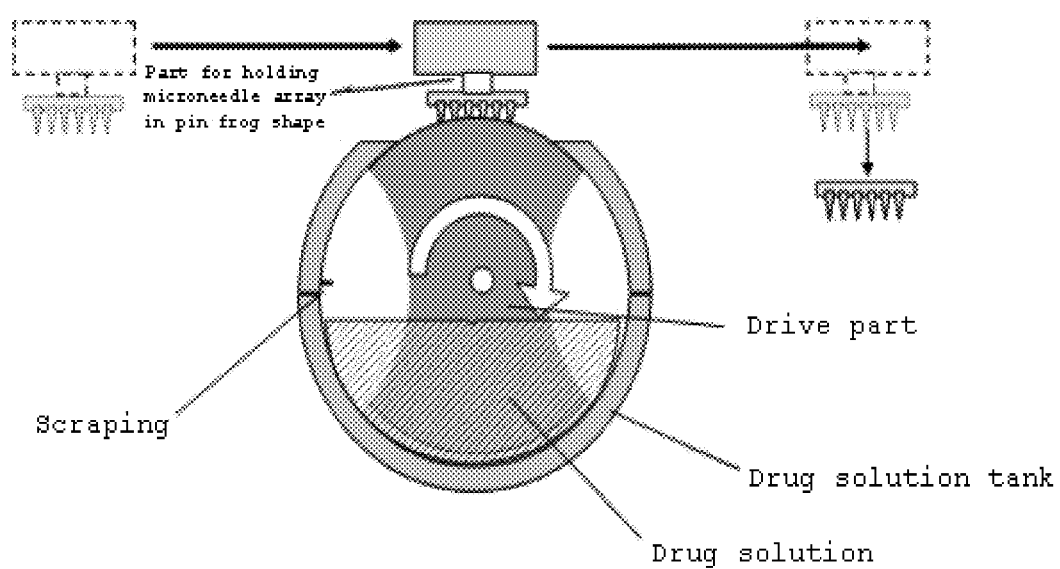
FIG. 5 is a schematic diagram representing a device used for preparing the microneedle array coated with the drug composition of the present invention.

The coater shown FIG. 5 (the volume of a drug aqueous solution: 4 ml) was used.

Immersion depth of microneedle array: about 300 µm

Figure 6:
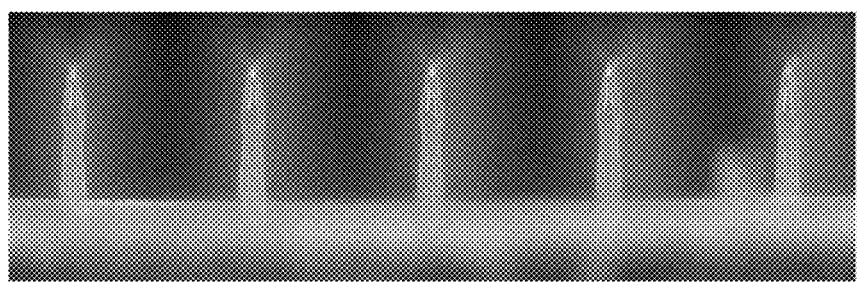
FIG. 6 is a side view (micrograph) of the microneedle array coated with the drug composition of the present invention (Example 2).

After coating said microneedle array with the solution, the microneedle array was dried at room temperature (20-25° C.) for 60 seconds. The step of the coating and the drying was repeated 5 times in total to provide the microneedle array shown in FIG. 6.

(3) Result

Figure 2:
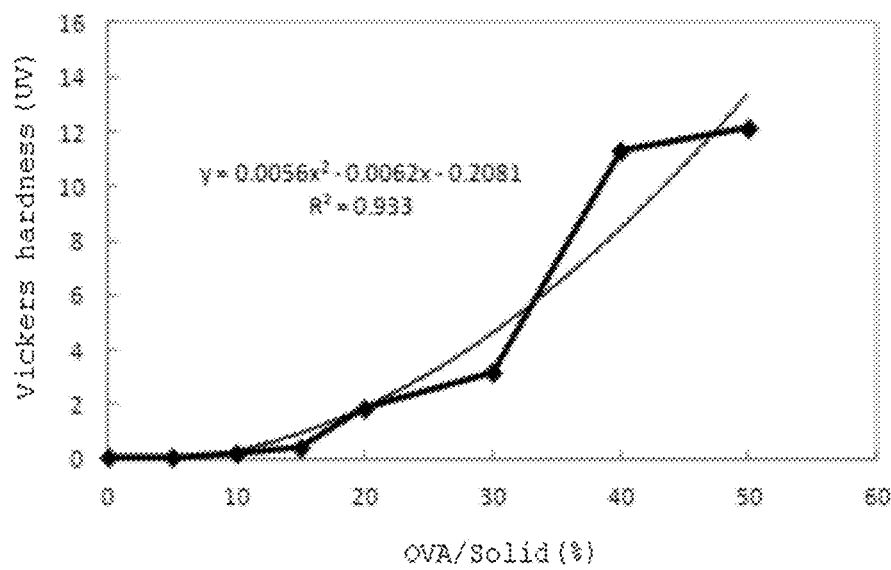
FIG. 2 is a diagram showing the correlation between the amount of OVA in the drug composition of the present invention (Example 2) and the Vickers hardness (the hardness) thereof.

As shown in FIG. 2, these results suggest that the Vickers hardness of the drug composition can increase (harden) with the increase in the amount of OVA. This result additionally supports the result of Example 1, and shows that the hardness of a drug composition can be improved by using proteins such as OVA.

Figure 3:
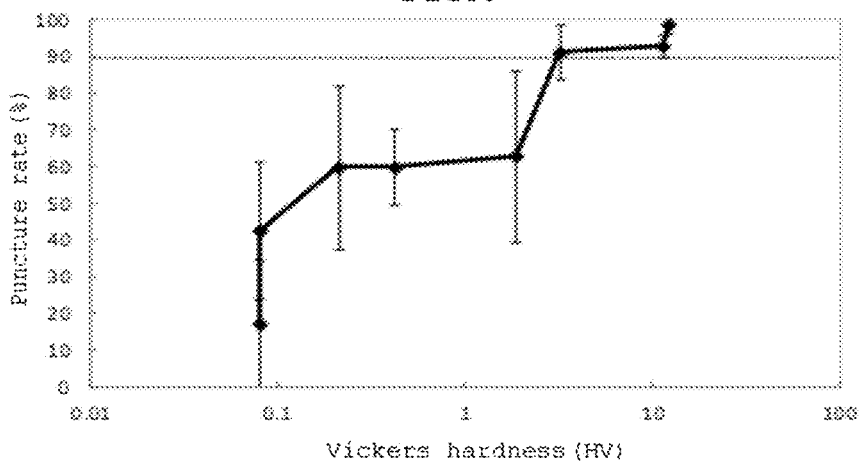
FIG. 3 is a diagram showing the correlation between the Vickers hardness (the hardness) of the drug composition of the present invention (Example 2) and the puncture rate of the microneedle array.

Furthermore, it was observed that the correlation between the Vickers hardness and the puncture rate of a drug composition had a tendency as shown in FIG. 3. Specifically, a Vickers hardness of 3 or more brought in a puncture rate of about 90%, and a Vickers hardness of 10 or more brought in a puncture rate of about 95% or more. Furthermore, when the Vickers hardness was 12 or more, most of drug compositions were not removed.

Example 3

Correlation Between Type of Additive (Difference in Molecular Weight) and Vickers Hardness (1) Reagent
   Drug: Lidocaine hydrochloride
   Additive: PVP (K-90), PVP (K-30), PVP (K-25), or CMCNa (Serogen P-815c)

(2) Method

Lidocaine hydrochloride was used as a drug, and each aqueous solution comprising a composition for coating was prepared according to the composition of Table 6 below. The prepared aqueous solution comprising each composition for coating was loaded on a preparation slide in a thin layer, and then dried at room temperature. The preparation slide after being dried was stored in the presence of silica gels. The hardness of the composition after being dried was measured with a micro-Vickers tester (MVK-G2500 manufactured by Akashi Seisakusho, Ltd.).

TABLE 6

| Lidocaine HCl | 10 | 10 | 10 | 10 | 10 | 10 | 10 | 10 | 10 | 10 | 10 | 10 | 0.6 | 2 | 6 | 0 |
|---|---|---|---|---|---|---|---|---|---|---|---|---|---|---|---|---|
| PVP (K-90) | | 30 | 10 | 5 | 10 | | | | | | | | | | | |
| PVP (K-30) | | | | | | 30 | 10 | 5 | 10 | | | | | | | |
| PVP (K-25) | | | | | | | | | | 30 | 10 | 5 | 10 | | | |
| CMCNa (P-815c) | | | | | | | | | | | | | | 2 | 2 | 2 | 2 |
| Purified water | 90 | 60 | 80 | 85 | 90 | 60 | 80 | 85 | 90 | 60 | 80 | 85 | 90 | 97.4 | 96 | 92 | 98 |

[NOTE]
PVP: Polyvinylpyrrolidone (Vickers hardness: about 12)
CMCNa: Sodium carboxymethylcellulose (Vickers hardness: about 7)

(3) Result

The measured Vickers hardness is shown in FIG. 4. Regarding PVP, the Vickers hardness tends to decrease as the molecular weight becomes smaller (K-90>K-30>K-25). Also, since the Vickers hardness of CMCNa is lower (softer) than that of PVP, the plasticity of the loaded drug composition becomes higher. Thus, it has suggested that the drug composition comprising CMCNa can be easily removed from the microneedle array when the microneedle array is punctured into the skin.

Example 4

Microneedle Array Coated with Composition Comprising Metoclopramide (1) Reagent a) As a solution of a hyaluronic acid composition comprising 10% metoclopramide, an aqueous solution consisting of 10 w/w % metoclopramide, 2 w/w % hyaluronic acid and 88 w/w % water is prepared.

b) As a solution of a collagen composition comprising 10% metoclopramide, an aqueous solution consisting of 10 w/w % metoclopramide, 2 w/w % hyaluronic acid, and 88 w/w % water is prepared.

(2) Coating Method and Evaluation Method a) According to Example 1, each metoclopramide solution in the above a) to b) is loaded on a separate glass plate and dried, and then the Vickers hardness of each solution is measured.

b) According to Example 2, each metoclopramide solution in the above a) to b) is loaded on a separate microneedle array, and a time-dependent change between the puncturability of the microneedle arrays and the blood levels of metoclopramide in a rat is evaluated. In order to measure the rat's blood levels, the six-week old male Wistar rat's abdomen is punctured with two pieces for each microneedles array coated with said two types of solutions. Blood sampling is performed at 0.5, 1, 2, 3, and 5 hours after the puncture while keeping each microneedle array on the abdomen with tape, and the blood levels of metoclopramide are measured.

After performing the blood sampling at 5 hours, the microneedle arrays are collected, and then the amounts of residual metoclopramide collected from Kimwipes® with which the skin surface is wiped and the collected microneedle arrays are measured.

(3) Result

The hyaluronic acid composition and the collagen composition which comprise metoclopramide have excellent Vickers hardness and puncturability, and also enable metoclopramide to be injected effectively into the skin.

Example 5

Evaluation about the Amount of Loaded Drug and the Transdermal Absorption Amount A microneedle array having 97 microneedles (the needle length is about 600 μm) per about 1 $cm^2$ was prepared according to the well-known method (WO 2012/057345), and then the following evaluation test on the amount of the loaded drug and the transdermal absorption amount was performed with the microneedle array.

(1) Reagent (Aqueous Solution of Composition for Coating)
   Additive: 0.5 w/w sodium carboxymethylcellulose (CMCNa) F1400MC+0.75 w/w % hydroxypropylcellulose 1000-5000 mPa·s
   Drug: 1 w/w % desmopressin acetate (Distribution Coefficient −3.18)
   Water: 97.75 w/w %

(2) Coating Method

The coater shown in FIG. 5 (the volume of a drug aqueous solution: 4 ml) was used.

Immersion depth of microneedle array: about 300 μm

After coating said microneedle array with the solution, the microneedle array was dried at room temperature (20-25° C.) for 60 seconds. The step of the coating and the drying was repeated 5 times in total to provide the microneedle array as shown in FIG. 7.

(3) Puncturing Method

The hair of the nine-week old male SD rat's abdomen was removed with a hair clipper and a shaver.

Figure 7:
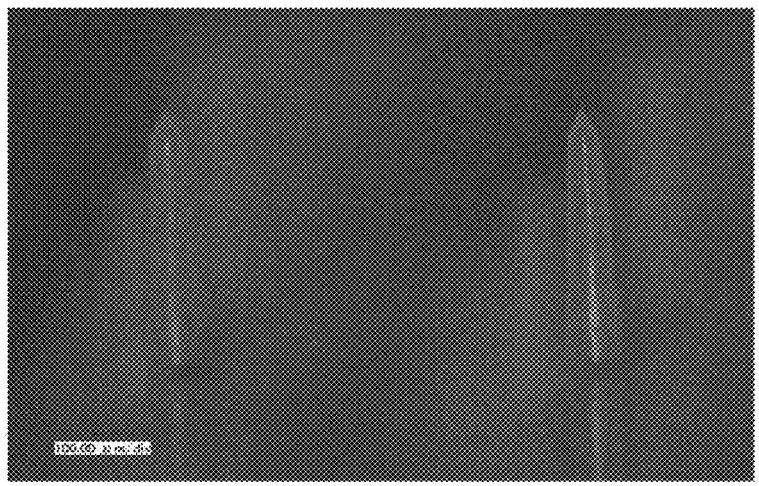
FIG. 7 is a side view (micrograph) of the microneedle array coated with the drug composition of the present invention (Example 5).

The microneedle array of FIG. 7 was pressed onto the rat's skin with a finger, and fixed with tape. After one hour, the microneedle array was removed.

In order to evaluate the amount of residual desmopressin acetate (the amount remained on the skin surface and the amount attached to the microneedle array), desmopressin acetate was collected as follows.

a) The Amount of Residual Desmopressin Acetate on the Skin Surface

The skin surface was wiped with Kimwipes® impregnated with ethanol, and the amount of the drug collected from the skin was investigated by measuring the drug in the Kimwipes® with a HPLC.

b) The Amount of Residual Desmopressin Acetate on the Surface of the Microneedle Array The collected microneedle array was immersed in 75% methanol, and the amount of the collected drug was measured with a HPLC.

(4) Result

The amounts (μg) of desmopressin acetate which attach and remain on the skin surface and the surface of the microneedle array were measured. The result is shown in Table 7.

TABLE 7

| Frequency of coating | Prior to use A | Needles after 1 hour adhesion C | Skin after 1 hour adhesion D | Amount of drug to be internally used E = A − (C + D) | Rate of drug to be internally used E/A*100 |
|---|---|---|---|---|---|
| 5 | 4.67 | <0.025 | <0.025 | >4.62 | >98.9 |
| 5 | 4.72 | <0.025 | <0.025 | >4.67 | >98.9 |
| 5 | 4.84 | <0.025 | <0.025 | >4.79 | >98.9 |
| 5 | 4.95 | <0.025 | <0.025 | >4.90 | >98.9 |
| 5 | 5.00 | <0.025 | <0.025 | >4.95 | >98.9 |
| 5 | 5.12 | <0.025 | <0.025 | >5.07 | >98.9 |

(Unit: μg)

The amount of the residual drug in the above Table 7 suggested that the composition for coating comprising desmopressin acetate could be administered under the skin at an extremely high rate.

Example 6

Comparative Evaluation of Drug Effects in Administration with Microneedle Array

The rate of desmopressin acetate to be internally used in Example 5 was separately confirmed by measuring the blood levels of desmopressin.

(1) Reagent

Microneedle array coated with desmopressin acetate: According to the method of Example 4, the step of the coating and the drying was performed to prepare the microneedle array on which about 5 μg of desmopressin acetate was loaded.

(2) Method

The hair of the nine-week old male SD rat's abdomen was removed with a hair clipper and a shaver. In the administration group with microneedle array, the microneedle array coated with desmopressin acetate was pressed onto the rat's skin with a finger, and fixed with protective tape. The blood sampling was performed at 5 minutes, 15 minutes, 30 minutes, 1 hour, and 2 hours after the drug administration, and the levels of desmopressin acetate in the rat's plasma were measured with a HPLC. For the administration group with microneedle array, after performing the blood sampling at 30 minutes after the administration, the microneedle array was removed, the skin surface was wiped with Kimwipes® impregnated with ethanol, and the amount of the drug collected from the skin was investigated by measuring the drug in the Kimwipes® with a HPLC. Also, the microneedle array after the administration was immersed in 75% methanol, and the amount of the collected drug was measured with a HPLC.

(3) Result

Figure 8:
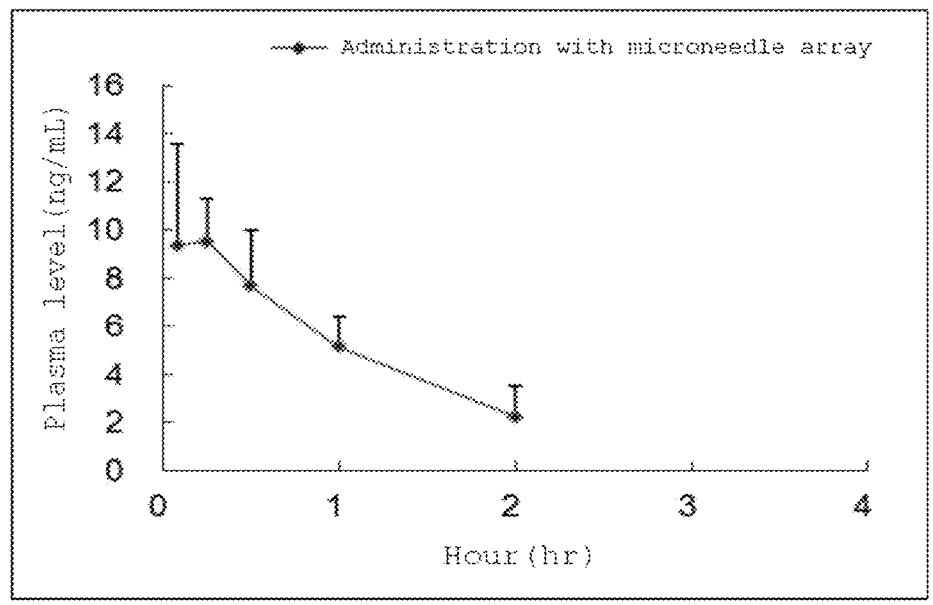
FIG. 8: The rat's abdominal skin was punctured with the microneedle array coated with desmopressin acetate of Example 5, and then the microneedle array was adhered to the skin and remained on the skin for 30 minutes. 99% of the loaded desmopressin acetate is injected into the skin by the transdermal administration of the microneedle array.

FIG. 8 shows the change in the rat's blood levels of desmopressin acetate after the administration with the microneedle array. Also, by correcting each parameter with the amounts of residual desmopressin acetate on the surface of the microneedle array and the like, each parameter can be organized as follows. The AUC value is also shown in FIG. 8 below.

TABLE 8

| Desmopressin acetate | Administration with microneedle array |
|---|---|
| Dosage (μg) | 4.88 |
| Amount remained on microneedle array | <0.025 |
| Amount remained on skin surface | <0.025 |
| Skin absorption amount | >4.83 |
| AUC after 5 hours: (ng · hr/mL) | 14.27 |

As shown in the above Table 8, about 99% of desmopressin acetate loaded on the microneedle array was injected into the skin 30 minutes after adhering the microneedle array to the skin. In addition, as shown in FIG. 8, desmopressin acetate rapidly transferred in the blood. Thus, the result shows that an effective subcutaneous administration can be achieved by using the microneedle array.

INDUSTRIAL APPLICABILITY

The microneedle array coated with the drug composition of the present invention can accurately insert the drug into the skin with little removal of the drug composition. Thus, even though the drug is present in a low concentration, the microneedle array of the present invention can be used for the administration of a drug such as a vaccine required to certainly administer a given amount of the drug into the skin. As a result, the drug administration with very little pain can be achieved by using the microneedle array of the present invention in place of conventional subcutaneous injection methods known as the administration of a protein or a vaccine.

The invention claimed is:

1. A microneedle array having a pin frog shape which is coated on a surface of microneedles with a drug composition comprising a drug and at least one additive, wherein:
the at least one additive is (i) an additive mixture comprising an adhesive additive having a Vickers hardness of less than 3 and an additive having a Vickers hardness of 10 or more which acts as a hardness-imparting additive, or (ii) an additive mixture comprising an adhesive additive having a Vickers hardness of less than 3 and an additive having a Vickers hardness of 3 to 10, the drug composition after being coated and dried has a Vickers hardness of 3 or more, the coated drug composition amount is 50 to 250 µg per 100 microneedles, wherein the drug composition does not cover the entire microneedles, and wherein an amount of the adhesive additive is 5 to 20 w/w % relative to a total amount of the additive mixture.

2. The microneedle array according to claim 1, wherein the drug composition after being coated and dried has a Vickers hardness of 10 or more.

3. The microneedle array according to claim 1, wherein the drug composition after being coated and dried has a Vickers hardness of 12 or more.

4. The microneedle array according to claim 1, wherein the additive having a Vickers hardness of 3 to 10 is sodium carboxymethylcellulose.

5. The microneedle array according to claim 1, wherein the adhesive additive having a Vickers hardness of less than 3 comprises at least one selected from the group consisting of hydroxypropylcellulose, sorbitol, and trehalose.

6. The microneedle array according to claim 1, wherein the additive having a Vickers hardness of 10 or more which acts as a hardness-imparting additive comprises at least one selected from the group consisting of dextran, gelatin, collagen, and hyaluronic acid.

7. The microneedle array according to claim 1, wherein the at least one additive comprises at least one selected from the group consisting of sugar or a derivative thereof, collagen, gelatin, and polyvinylpyrrolidone.

8. The microneedle array according to claim 7, wherein the sugar or the derivative thereof is at least one selected from the group consisting of hydroxypropylcellulose, sodium carboxymethylcellulose, hyaluronic acid, trehalose, lactose, sucrose, sorbitol, pullulan, and dextran.

9. The microneedle array according to claim 1, wherein the drug is a peptide, a protein, a nucleic acid, or RNA.

10. The microneedle array according to claim 1, wherein the drug is a vaccine.

11. The microneedle array according to claim 1, wherein an amount of the drug in the drug composition is 25 w/w % or less.

12. The microneedle array according to claim 1, wherein the at least one additive is (i) the additive mixture comprising an adhesive additive having a Vickers hardness of less than 3 and an additive having a Vickers hardness of 10 or more which acts as a hardness-imparting additive.

13. The microneedle array according to claim 1, wherein the at least one additive is (ii) the additive mixture comprising an adhesive additive having a Vickers hardness of less than 3 and an additive having a Vickers hardness of 3 to 10.

14. The microneedle array according to claim 1, wherein a length of the microneedles is from 300 to 1000 µm.

15. The microneedle array according to claim 1, wherein a length of the microneedles is about 600 µm, and the drug composition covers the microneedles from a tip to about 300 µm therefrom.

16. The microneedle array according to claim 1, wherein the microneedle array has from 50 to 200 microneedles per $cm^2$.

17. The microneedle array according to claim 1, wherein the coated drug composition amount is from 50 to 200 µg per 100 microneedles.

18. The microneedle array according to claim 1, wherein the coated drug composition amount is from 50 to 100 µg per 100 microneedles.

* * * * *